(12) United States Patent
Sato

(10) Patent No.: US 8,052,942 B2
(45) Date of Patent: Nov. 8, 2011

(54) ANALYTICAL TOOL CARTRIDGE WITH RETRIEVAL MECHANISM, AND SET OF THE CARTRIDGE AND ANALYZER

(75) Inventor: Yoshiharu Sato, Kyoto (JP)

(73) Assignee: Arkray, Inc. (JP)

( * ) Notice: Subject to any disclaimer, the term of this patent is extended or adjusted under 35 U.S.C. 154(b) by 2126 days.

(21) Appl. No.: 10/511,588

(22) PCT Filed: Apr. 4, 2003

(86) PCT No.: PCT/JP03/04373
§ 371 (c)(1),
(2), (4) Date: Oct. 4, 2004

(87) PCT Pub. No.: WO03/085392
PCT Pub. Date: Oct. 16, 2003

(65) Prior Publication Data
US 2005/0186162 A1    Aug. 25, 2005

(30) Foreign Application Priority Data
Apr. 5, 2002    (JP) ................................ 2002-104274

(51) Int. Cl.
*B01L 3/00* (2006.01)
(52) U.S. Cl. ........................................ 422/430
(58) Field of Classification Search .................... 422/104
See application file for complete search history.

(56) References Cited

U.S. PATENT DOCUMENTS

| 3,918,910 A | 11/1975 | Soya et al. |
| 4,911,344 A | 3/1990 | Kahler |
| 5,320,732 A | 6/1994 | Nankai et al. |
| 5,395,504 A | 3/1995 | Saurer et al. |
| 5,854,074 A | 12/1998 | Charlton et al. |
| 5,872,713 A | 2/1999 | Douglas et al. |
| 6,176,119 B1 | 1/2001 | Kintzig |
| 2003/0013992 A1 | 1/2003 | Uchigaki et al. |

FOREIGN PATENT DOCUMENTS

| DE | 42 05 805 | 9/1993 |
| EP | 1147739 A2 * | 10/2001 |
| JP | 4-357449 | 12/1992 |
| JP | 6-294769 | 10/1994 |
| JP | 8-94630 | 4/1996 |
| JP | 8-262026 | 10/1996 |

(Continued)

*Primary Examiner* — Bobby Ramdhanie
(74) *Attorney, Agent, or Firm* — Studebaker & Brackett PC; Donald R. Studebaker

(57) ABSTRACT

The present invention relates to an analytical tool cartridge comprising a case having therein a storage space and a retrieval port that communicates the storage space with an external space, and a plurality of analytical tools stored in the storage space in a stacked state. This analytical tool cartridge further has a retrieval mechanism for retrieving the analytical tools one at a time from the case via the retrieval port. The analytical tool cartridge may also further have an opening/closing mechanism for opening and closing the retrieval port. The present invention also provides a set of the analytical tool cartridge, and an analyzer that is constituted so as to have installed therein an analytical tool retrieved from the analytical tool cartridge, and analyze a specific component in a specimen liquid supplied onto the analytical tool. At least one of the analytical tool cartridge and the analyzer has provided therein cartridge fixing means for locating and fixing the analytical tool cartridge onto the analyzer.

16 Claims, 10 Drawing Sheets

FOREIGN PATENT DOCUMENTS

| | | |
|---|---|---|
| JP | 9-250998 | 9/1997 |
| JP | 10-253570 | 9/1998 |
| JP | 2001-141686 | 5/2001 |
| JP | 2001-281199 | 9/2001 |
| JP | 2003-42994 | 2/2003 |
| JP | 2003-139777 | 5/2003 |
| WO | WO 9410558 A1 * | 5/1994 |
| WO | WO 99/22236 | 5/1999 |
| WO | WO 01/63272 | 8/2001 |
| WO | WO 02/08753 | 1/2002 |
| WO | WO 0218940 A2 * | 3/2002 |
| WO | WO 02055008 A2 * | 7/2002 |

* cited by examiner

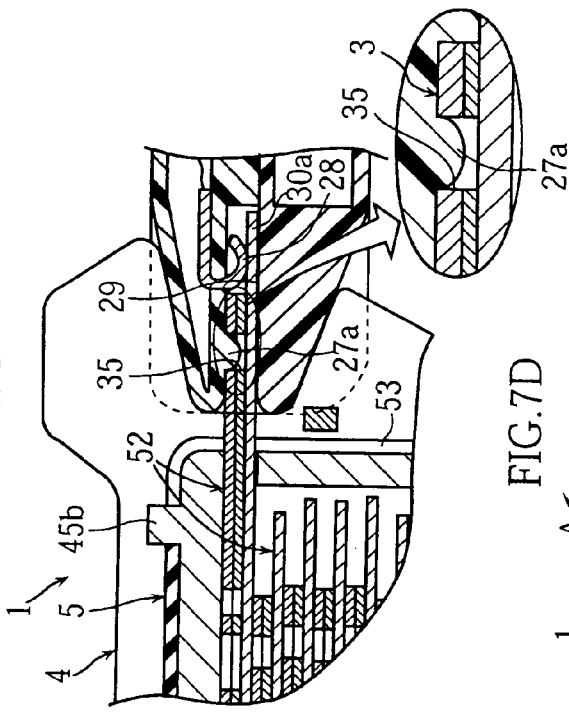
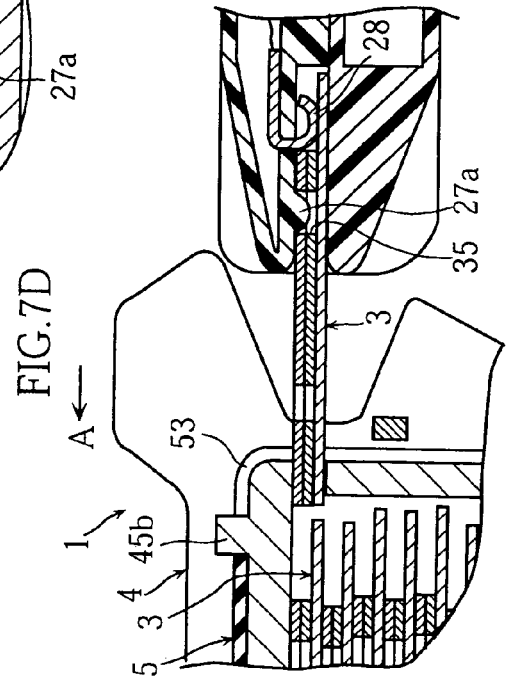
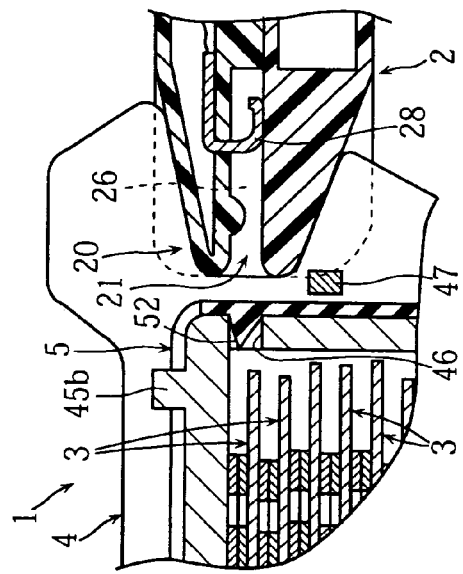
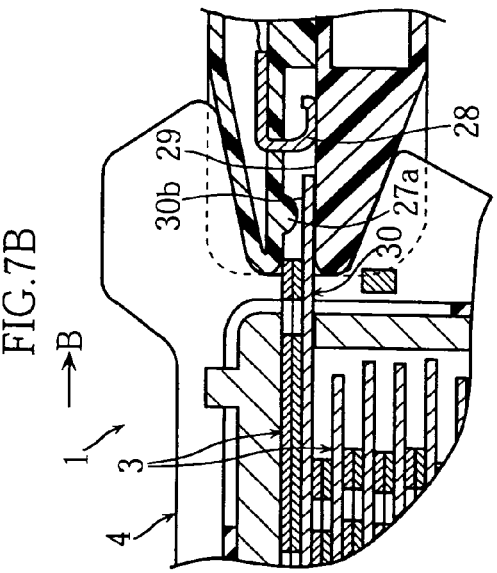

ANALYTICAL TOOL CARTRIDGE WITH RETRIEVAL MECHANISM, AND SET OF THE CARTRIDGE AND ANALYZER

TECHNICAL FIELD

The present invention relates to an analytical tool cartridge in which are stored a plurality of analytical tools.

The present invention also relates to a set of the analytical tool cartridge, and an analyzer that is constituted so as to analyze a specific component in a specimen liquid with an analytical tool installed therein.

BACKGROUND ART

A common method of measuring the concentration of a specific component in a body fluid, for example glucose in blood, uses a redox reaction with an oxidoreductase as a catalyst. Moreover, simple blood sugar level measuring apparatuses of a size that will fit in the palm of the hand have become widely used so that blood sugar level can be measured easily at home, at a travel destination, and soon. With such a simple blood sugar level measuring apparatus, for example, as described in Japanese Patent Application Laid-open No. 4-357449, a biosensor that provides an enzyme reaction site and is constituted so as to be disposable is installed in the apparatus, and then blood is supplied onto this biosensor, whereby the blood sugar level is measured.

As shown in FIG. 11, the installation of the biosensor 91 into the simple blood sugar level measuring apparatus 90 is generally carried out by the user holding the biosensor 91, and inserting the biosensor 91 into an insertion port 92 of the simple blood sugar level measuring apparatus 90. With such a biosensor 91 installation method, there have been the following problems.

The biosensors 91 are each sold, for example, in a state individually housed in packaging comprising a laminated aluminum sheet. In this case, to install a biosensor 91 in the simple blood sugar level measuring apparatus 90, first the biosensor 91 must be removed from the packaging. This operation must be carried out every time the blood sugar level is to be measured, which is troublesome, and is inconvenient in particular for people with failing eyesight or elderly people.

The biosensor 91 is of a chip shape with a width dimension of approximately 0.5 to 1 cm and a length dimension of approximately 2 to 5 cm, and the insertion port 92 of the simple blood sugar level measuring apparatus 90 has an opening portion of a size corresponding to the cross section of the biosensor 91. The operation of inserting the biosensor 91 into the insertion port 92 is thus not necessarily easy, being inconvenient in particular for people with failing eyesight or elderly people.

DISCLOSURE OF THE INVENTION

It is an object of the present invention to make it possible to install an analytical tool in an analyzer through a simple operation.

An analytical tool cartridge provided according to a first aspect of the present invention is an analytical tool cartridge comprising a case having therein a storage space and a retrieval port that communicates the storage space with an external space, and a plurality of analytical tools stored in the storage space in a stacked state, the analytical tool cartridge further comprising a retrieval mechanism for retrieving the analytical tools one at a time from the case via the retrieval port.

The analytical tool cartridge preferably further comprises an opening/closing mechanism for opening and closing the retrieval port, this being to prevent dust and moisture from infiltrating in via the retrieval port. The retrieval mechanism and the opening/closing mechanism may be constituted from a single operating body. In this case, the operating body is made to comprise an engaging projection for integrally moving one of the analytical tools upon the operating body being moved in a specific direction from a standby state, a closing portion that closes up the retrieval port in the standby state, and an opening portion that opens up the retrieval port upon the operating body being moved in the specific direction from the standby state. The operating body preferably further has an operating portion for making moving the operating body easy.

The case has, for example, an annular wall portion that defines the storage space and has the retrieval port provided therein. In this case, the operating body is formed in a loop, is disposed along an outer surface of the annular wall portion, and is constituted so as to be movable relative to the annular wall portion.

Each of the analytical tools preferably has an engaging portion with which the engaging projection engages. This engaging portion is constituted from a recess or a projection provided in or on the analytical tool. In the case that the analytical tool has a capillary, an air release port communicating with the capillary may be used as the engaging portion.

The storage space in the case preferably has a desiccant housed therein in advance. As a result, the storage space is dehumidified, and hence degradation of the analytical tools by humidity is suppressed. It is preferable to dehumidify the storage space in particular in the case that the analytical tools have a reagent layer containing an enzyme or the like.

The analytical tools are, for example, stored in the storage space in a state supported by a platform. In this case, the desiccant is fixed to the platform. The fixing of the desiccant is carried out, for example, by kneading the desiccant in the form of granules together with a resin material, thus dispersing the desiccant in the resin, or by attaching a desiccant powder to the surface of the platform.

In the case that the analytical tools are supported by a platform, the analytical tools are preferably supported in a biased state. The bias of the analytical tools is carried out, for example, using a coil spring, a leaf spring, or an elastic body such as a foam or rubber.

As described above, the operating body moves relative to the case; a guiding portion for guiding the operating body during this movement is preferably provided on the case. The guiding portion is, for example, constituted as a groove or projection provided in or on the case.

It is preferable, for example, for the storage space to have therein stacked on top of the analytical tools an information outputting chip from which can be outputted information relating to properties of the analytical tools. Examples of the information outputted from the information outputting chip include information relating to the sensitivity of the analytical tools (information necessary for selecting a calibration curve in the analyzer), and individual information on the analytical tools (date of manufacture, time limit for usage, manufacturer, location of manufacture (country, factory), etc.).

If such an information outputting chip is housed uppermost in the storage space in advance, then the information outputting chip will be retrieved from the analytical tool cartridge first. Consequently, when the analytical tool cartridge is used, the analyzer can be made aware of information relating to the properties of the analytical tools first. For example, in the case that the information from the information outputting chip is information necessary for selecting a calibration curve, the possibility of one neglecting to select the calibration curve is reduced. With this method of selecting the calibration curve, there is also no need for a user to carry out a troublesome operation such as carrying out a button operation on the analyzer, and hence the burden on the user when selecting the calibration curve can be reduced.

In a second aspect of the present invention, there is provided a set of the analytical tool cartridge according to the first aspect of the present invention as described above, and an analyzer that is constituted so as to have installed therein an analytical tool retrieved from the analytical tool cartridge, and analyze a specific component in a specimen liquid supplied onto the analytical tool, wherein the analytical tool cartridge and the analyzer have provided therein cartridge fixing means for locating and fixing the analytical tool cartridge onto the analyzer.

The cartridge fixing means is, for example, constituted so as to have first stopper faces for restricting movement of the analytical tool cartridge in a direction orthogonal to each of a direction of stacking of the analytical tools and a direction of insertion of the analytical tools, and second stopper faces for restricting movement of the analytical tool cartridge in the direction of stacking of the analytical tools.

The first stopper faces are, for example, provided on the analyzer, and the second stopper faces are, for example, provided on the analytical tool cartridge. More specifically, the cartridge fixing means is, for example, constituted from notches provided in the case, and recessed portions provided in the analyzer.

In a third aspect of the present invention, there is provided a set of the analytical tool cartridge according to the first aspect of the present invention as described above, and an analyzer that is constituted so as to have installed therein an analytical tool retrieved from the analytical tool cartridge, and analyze a specific component in a specimen liquid supplied onto the analytical tool, wherein the analyzer has an inserting portion into which an end portion of the analytical tool is inserted, and the analytical tool cartridge and the inserting portion have provided therein analytical tool fixing means for fixing the analytical tool in the analyzer.

The analytical tool fixing means comprises, for example, a projection that is provided on one of the analytical tool and the inserting portion, and a recess that is provided in the other thereof and engages with the projection.

BRIEF DESCRIPTION OF THE DRAWINGS

FIGS. 7A to 7D are sectional views of main parts for explaining an operation of installing a biosensor into the analyzer from the sensor cartridge.

BEST MODE FOR CARRYING OUT THE INVENTION

Following is a concrete description of best modes for carrying out the present invention, with reference to the drawings.

Figure 1:
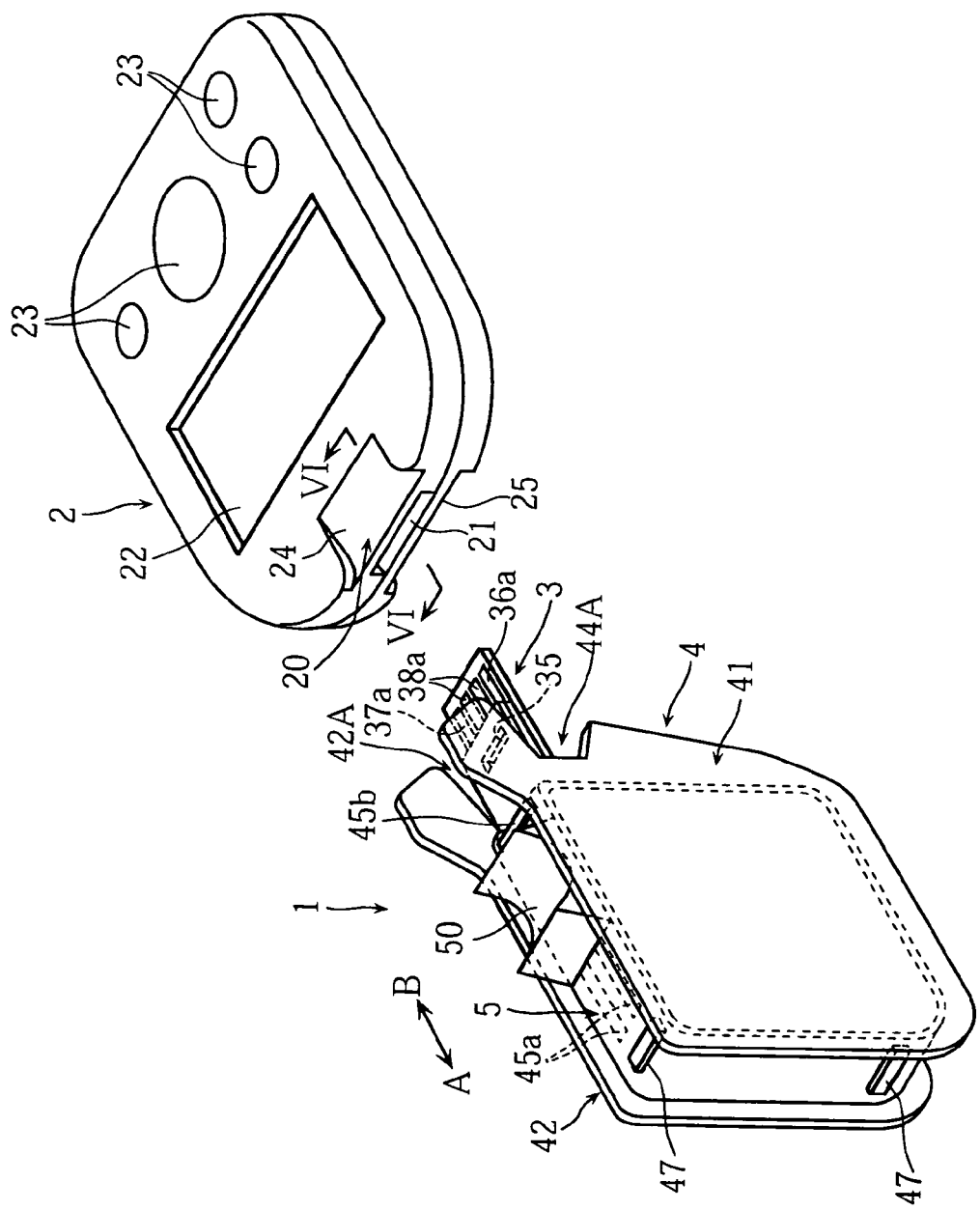
FIG. 1 is an overall perspective view for explaining an example of a set of an analyzer and a sensor cartridge according to the present invention.

FIG. 1 shows a set of a sensor cartridge 1 and an analyzer 2 according to the present invention.

Figure 2:
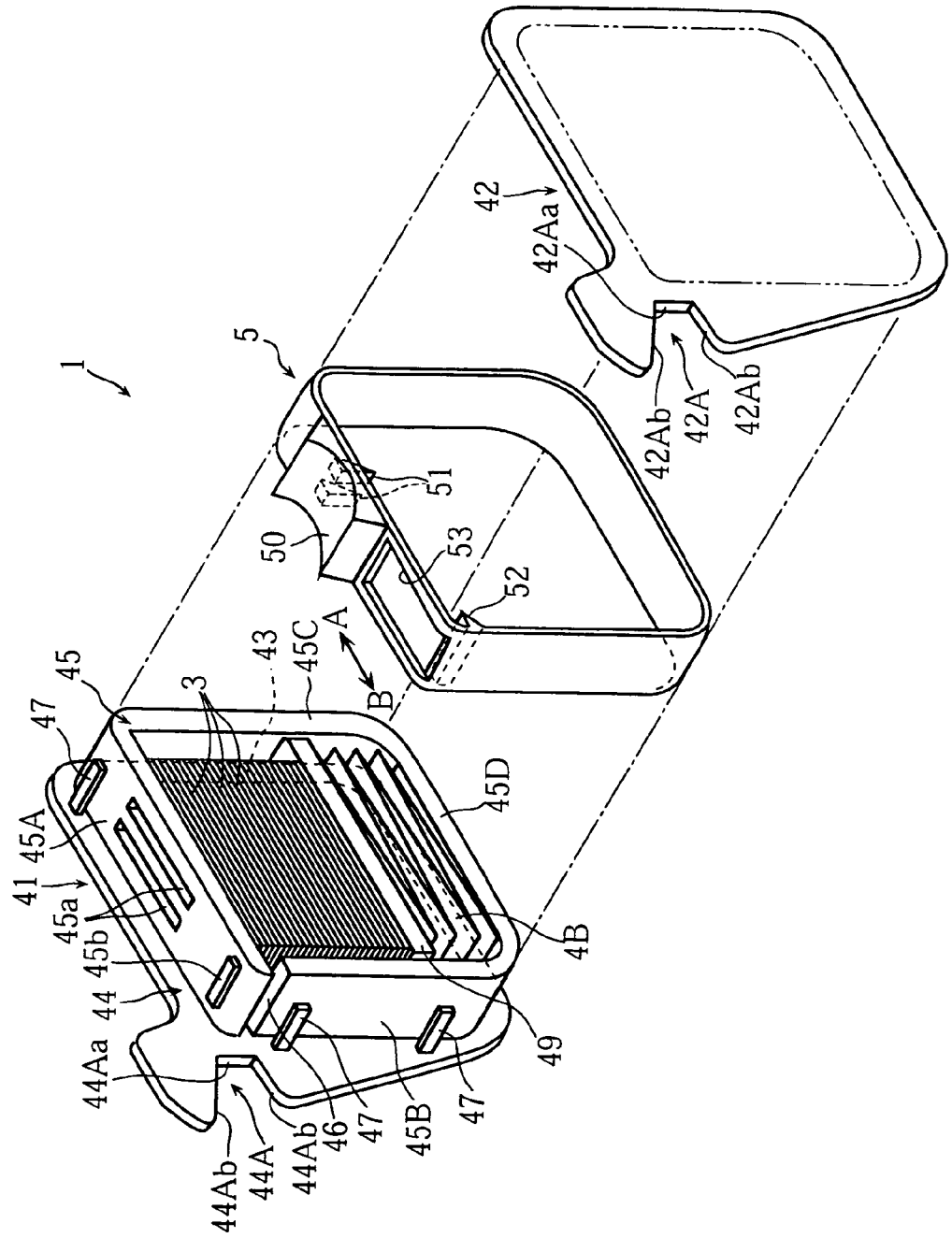
FIG. 2 is an exploded perspective view of the sensor cartridge shown in FIG. 1.

As shown in FIG. 2, the sensor cartridge 1 holds a plurality of biosensors 3, and is constituted such that the biosensors 3 can be retrieved one at a time. As shown in FIGS. 1 and 2, the sensor cartridge 1 has a case 4, and an operating belt 5 that moves (rotates) relative to the case 4.

The case 4 has first and second members 41 and 42 that are formed, for example, by resin molding, and a storage space 43 for storing the plurality of biosensors 3 is formed through the first and second members 41 and 42 being joined together.

The first member 41 has a plate-shaped portion 44 and an annular wall portion 45. The plate-shaped portion 44 has a notch 44A provided therein. The second member 42, on the other hand, has a form similar to that of the plate-shaped portion 44 of the first member 41. That is, the second member 42 also has a notch 42A therein. Each of the notches 42A and 44A has a base face 42Aa or 44Aa and two tapering faces 42Ab or 44Ab, and has a shape that progressively opens out toward the outside. As will be described later with reference to FIGS. 6 and 7, these notches 42A and 44A are used to locate and fix the sensor cartridge 1 onto the analyzer 2 when a biosensor 3 retrieved from the sensor cartridge 1 is to be installed in the analyzer 2.

The annular wall portion 45 of the first member 41 projects out from a peripheral portion of the plate-shaped portion 44 in the thickness direction of the plate-shaped portion 44, and has an upper wall portion 45A, side wall portions 45B and 45C, and a bottom wall portion 45D. A slit 46 is provided between the upper wall portion 45A and the side wall portion 45B. This slit 46 communicates the storage space 43 with the outside, and is for retrieving an uppermost biosensor 3 out to the outside when this biosensor 3 is moved in the direction of the arrow B in the drawings. A plurality of projections 47 are provided on a periphery of the annular wall portion 45. These projections 47 have a function of guiding the operating belt 5 when the operating belt 5 is rotated. Such projections 47 may also be provided on the second member 42, or the guiding function may alternatively be achieved by providing grooves in the first or second member 41 or 42.

The upper wall portion 45A has two slits 45a provided therein, and has a stopper 45b provided thereon. The slits 45a extend in the direction of the arrows A and B in the drawings, and penetrate through the upper wall portion 45A. Engaging claws 51 of the operating belt 5, described later, are passed through the slits 45a, and movement of these engaging claws 51 in the direction of the arrows A and B is permitted by the slits 45*a*. The stopper 45*b* extends in the thickness direction of the plate-shaped portion 44, and restricts the movement of the operating belt 5.

A platform 49 that is supported by a spring 48 fixed to the bottom wall portion 45D is housed in the storage space 43. This platform 49 is biased by the spring 48 toward the upper wall portion 45A side. The plurality of biosensors 3 are sandwiched in a stacked state between the platform 49 and the upper wall portion 45A by the resiliency of the spring 48. The plurality of biosensors 3 are thus held in the storage space 43, i.e. inside the case 4.

Note that a constitution may be adopted in which, when the sensor cartridge 1 is shipped out, there is a calibrating chip (omitted from the drawings) housed on top of the plurality of biosensors 3, and this calibrating chip is retrieved first. Here, the calibrating chip is, for example, used, in the case that the analyzer 2 stores data for a plurality of calibration curves, for selecting the calibration curve from out of these calibration curves that best fits the sensitivity of the biosensors 3. Consequently, if it is made to be such that that the calibrating chip is retrieved first when using the sensor cartridge 1, then the possibility of one neglecting to select the calibration curve using the calibrating chip is reduced. Moreover, if it is made to be such that the calibration curve is selected using such a calibrating chip, then the necessity of carrying out a troublesome operation (for example a button operation carried out by a user on the analyzer 2 when selecting the calibration curve) is eliminated, and hence the burden on the user when selecting the calibration curve can be reduced.

As the platform 49, it is preferable to use one having a dehumidifying function. As a result, even in the case that the biosensors 3 are prone to being degraded by humidity, this can be suppressed. As such a platform 49, for example, one obtained by kneading together a thermoplastic resin and a powder of a desiccant such as silica and then molding, one obtained by attaching a desiccant in the form of a powder or the like to a plate of a resin, a metal or the like, or one obtained by fixing a desiccant into a porous body can be used. In the case that the platform 49 is not given a dehumidifying function, it is preferable to put a desiccant into the storage space 43 in advance.

The spring 48 is, for example, constituted as a leaf spring, and is integrated with the first member 41. The spring 48 is integrally molded with the first member 41 when molding the first member 41, or else a leaf spring formed as a separate member is integrated with the first member 41 by insert molding when molding the first member 41. Note, however, that from the viewpoint of operability and manufacturing cost, the spring 48 is preferably integrally molded with the first member 41. A coil spring, or an elastic body of a resin foam, a rubber or the like can of course be used instead of a leaf spring.

Figure 3:
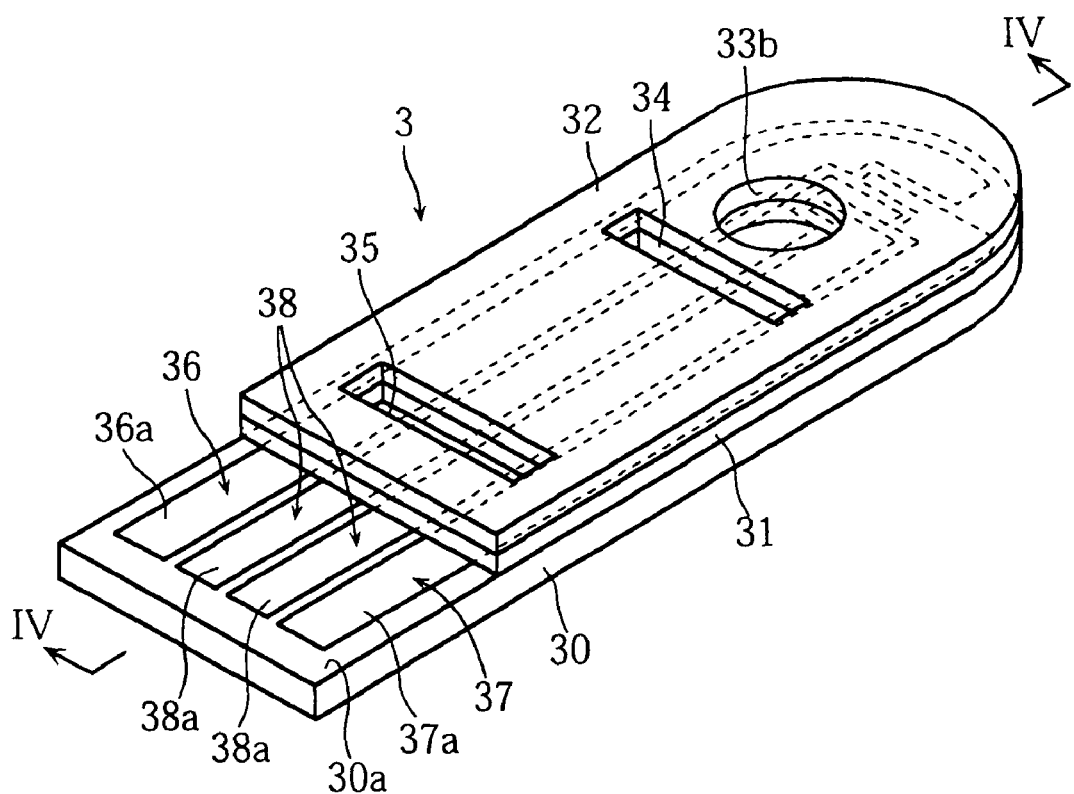
FIG. 3 is an overall perspective view of a biosensor shown in FIG. 2.
Figure 4:
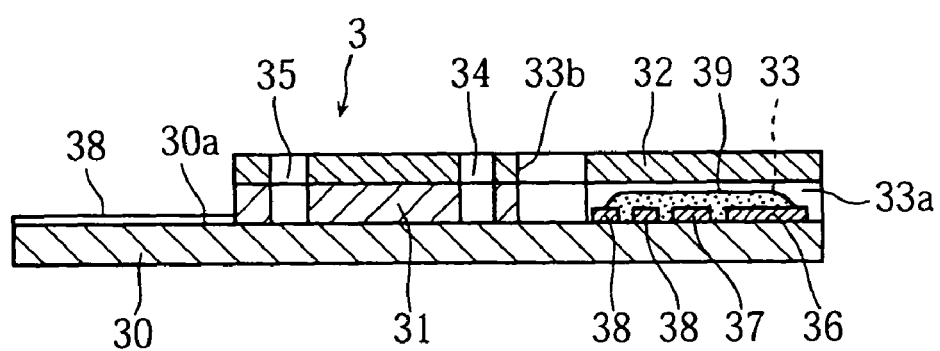
FIG. 4 is a sectional view along line IV-IV in FIG. 3.

As shown clearly in FIGS. 3 and 4, each biosensor 3 has a constitution in which a cover 32 is attached to a substrate 30 via spacer 31. The biosensor 3 has a channel 33 formed therein between the substrate 30 and the cover 32. This channel 33 is communicated to the outside via a specimen introduction port 33*a* and an air release port 33*b*. The biosensor 3 further has provided therein two recesses 34 and 35 that each extend in the width direction of the substrate 30. The recess 34 is used when moving the biosensor 3 together with the operating belt 5 as described later with reference to FIG. 5. The recess 35, on the other hand, is used when installing the biosensor 3 in the analyzer 2 as described later with reference to FIGS. 7C and D. Note that the recesses 34 and 35 penetrate through both the spacer 31 and the cover 32 here, but do not necessarily have to be formed so as to penetrate through both the spacer 31 and the cover 32.

An upper surface 30*a* of the substrate 30 has provided thereon a working electrode 36, a counter electrode 37, a pair of detecting electrodes 38 (hereinafter these are sometimes referred to collectively as the 'electrodes 36 to 38'), and a reagent layer 39.

The working electrode 36 and the counter electrode 37 are used, for example, for measuring the amount of electrons supplied from the reagent layer 39 as a response current when a fixed potential is applied to the reagent layer 39. On the other hand, the pair of detecting electrodes 38 are used to judge whether or not blood has been introduced into the channel 33 of the biosensor 3. One end portion 36*a*, 37*a* or 38*a* of each of the electrodes 36 to 38 is not covered by the spacer 31 or the cover 32, but rather is exposed. These end portions 36*a*, 37*a* and 38*a* constitute terminal portions for contacting with terminals 28 of the analyzer 2, described later (see FIGS. 6 and 7).

The reagent layer 39 is, for example, solid, and is formed so as to cover the electrodes 36 to 38. The reagent layer 39 comprises, for example, a relatively small amount of an oxidoreductase dispersed in a relatively large amount of a mediator (an electron transporter). An iron complex or a ruthenium complex can, for example, be used as the electron transporter. The oxidoreductase is selected in accordance with the type of the specific component that is to be subjected to the concentration measurement. Examples of the specific component include glucose, cholesterol and lactic acid. Examples of oxidoreductases for such specific components include glucose dehydrogenase, glucose oxidase, cholesterol dehydrogenase, cholesterol oxidase, lactic acid dehydrogenase, and lactic acid oxidase.

Figure 5B:
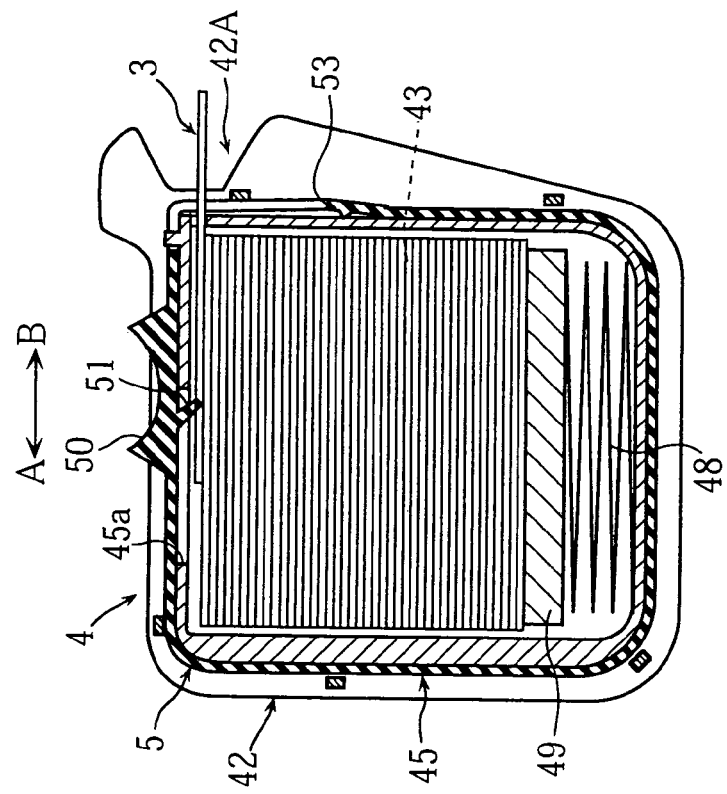
FIGS. 5A and 5B are sectional views for explaining an operation of retrieving a biosensor from the sensor cartridge.
Figure 5A:
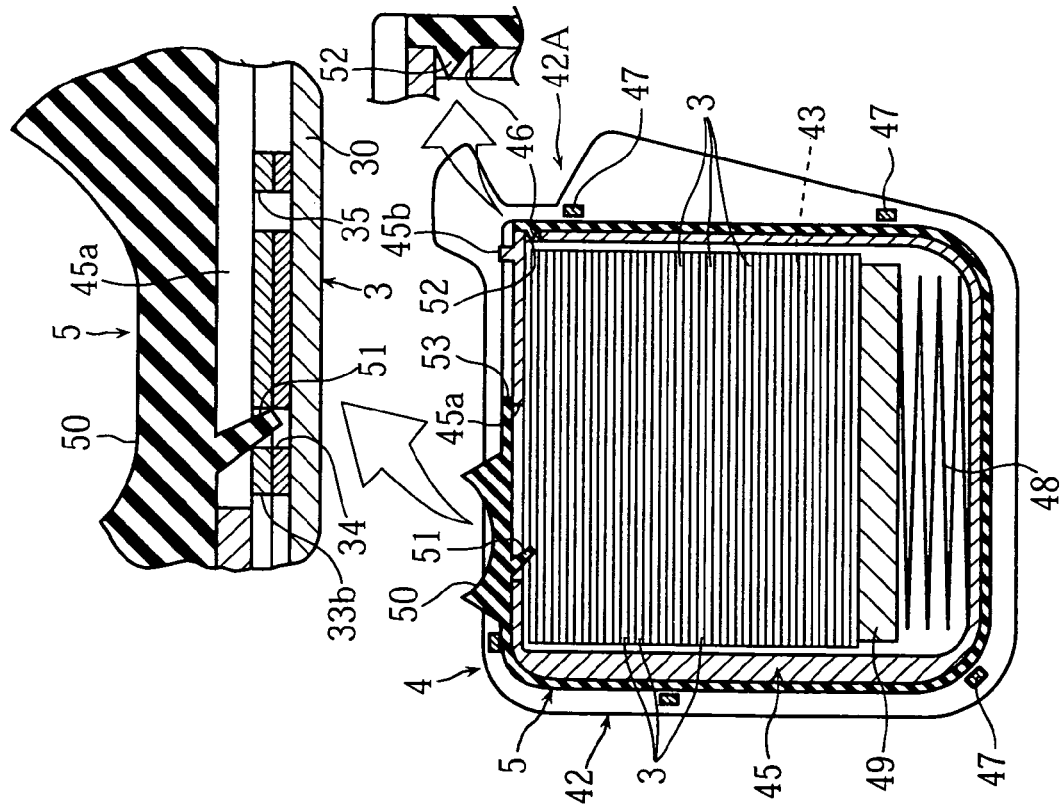

As shown in FIGS. 1, 2 and 5A, the operating belt 5 has the form of a loop overall, and is stretched around an outer surface of the annular wall portion 45 of the first member 41. The operating belt 5 has thereon a knob 50, the pair of engaging claws 51, a closing portion 52, and an opening portion 53.

The knob 50 is for moving (rotating) the operating belt 5 relative to the annular wall portion 45, and hence the case 4, along the outer surface of the annular wall portion 45.

The pair of engaging claws 51 are passed through the slits 45*a* in the upper wall portion 45A of the annular wall portion 45, with ends thereof that project out through the slits 45*a* engaging into the recess 34 in a biosensor 3. Upon operating the knob 50, the pair of engaging claws 51 move through the slits 45*a*, and at the same time move relative to the upper wall portion 45A. At this time, because the engaging claws 51 are engaged into the recess 34, through the operation of the knob 50, the biosensor 3 is also moved relative to the annular wall portion 45, and hence the case 4. The number and shape of the engaging claws 51 is not limited to being as in the example shown in the drawings, but rather design modification is possible.

The closing portion 52 closes up the slit 46 in the annular wall portion 45 in a standby state (a state when a biosensor 3 is not to be retrieved). As a result, the storage space 43 in the case 4 is kept airtight in the standby state, whereby degradation of the biosensors 3 by moisture, and short-circuiting between the electrodes 36 to 38 of each of the biosensors 3 due to dust and so on are suppressed.

The opening portion 53 is for opening up the slit 46 in the annular wall portion 45 when the operating belt 5 is moved relative to the annular wall portion 45 as shown in FIG. 5B, i.e. when a biosensor 3 is moved. As a result, the biosensor 3 held in the storage space 43 can be discharged out from the storage space 43. When the stopper 45*b* of the case 4 is positioned in the opening portion 53, and the stopper 45b and an edge defining the opening portion 53 interfere with one another through the movement of the operating belt 5, the movement of the operating belt 5 is restricted.

With the sensor cartridge 1 having the above constitution, in the standby state, as shown in FIG. 5A, the engaging claws 51 of the operating belt 5 are engaged in the recess 34 of the uppermost biosensor 3, and moreover the biosensor 3 is biased upward. As a result, it is made to be such that upon moving the operating belt 5, only the uppermost biosensor 3 can move relative to the case 4. Moreover, the slit 46 in the case 4 is closed up by the closing portion 52 of the operating belt 5. As a result, the inside of the case 4 is kept airtight in the standby state.

As shown in FIG. 5B, if the knob 50 is operated and moved in the direction of the arrow B in the drawings, then the engaging claws 51 and the closing portion 52 move in the direction of the arrow B together with the knob 50. At this time, the operating belt 5, while being guided by the plurality of projections 47 on the case 4, moves (rotates) along the outer surface of the annular wall portion 45. When the operating belt 5 is rotated, the closing portion 52 moves away from the slit 46, and the opening portion 53 of the operating belt 5 comes to be positioned at the slit 46, whereby the storage space 43 is communicated to the outside. Moreover, because the engaging claws 51 are engaged in the recess 34 of the biosensor 3, upon the engaging claws 51 moving in the direction of the arrow B, the biosensor 3 also moves in the direction of the arrow B. Because the biosensors 3 are biased upward, and the slit 46 is opened up by the movement of the knob 50, one biosensor 3 only is discharged from the slit 46. At this time, because the biosensors 3 are biased upward in the case 4, all of the plurality of biosensors 3 move upward, the biosensor 3 has been completely discharged from the case 4, the knob 50 is then moved in the direction of the arrow A so as to move into the standby state shown in FIG. 5A. As a result, the engaging claws 51 of the operating belt 5 are engaged into the recess 34 of the biosensor 3 that is now uppermost, and hence the standby state is achieved.

Figure 6:
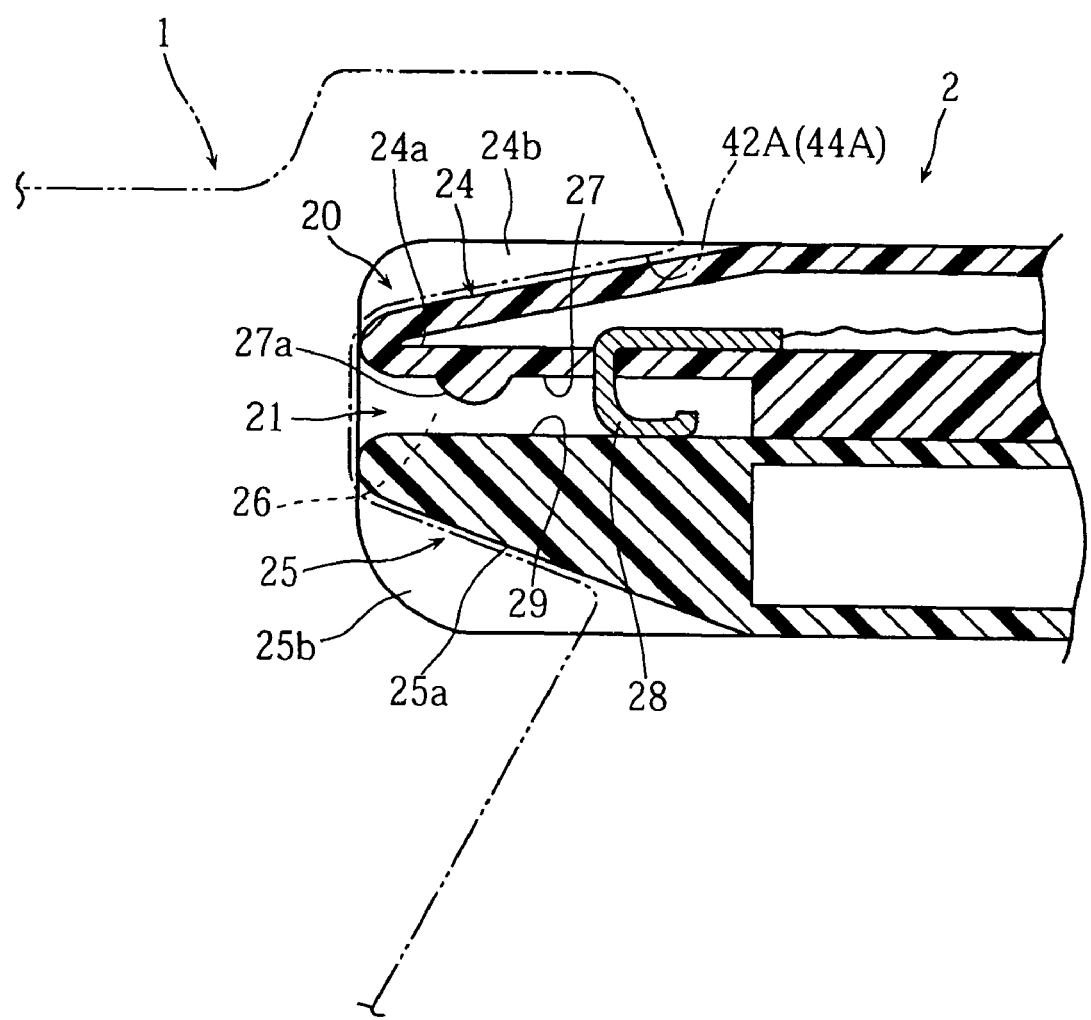
FIG. 6 is a sectional view along line VI-VI in FIG. 1.

As shown in FIGS. 1 and 6, the analyzer 2 is constituted, for example, so as to measure the concentration of a specific component in a specimen liquid supplied onto a biosensor 3 using an electrochemical method. This analyzer 2 comprises a holding portion 20 onto which the sensor cartridge 1 can be located and fixed, and an inserting portion 21 for inserting a biosensor 3, and also has a display 22 and operating buttons 23.

The holding portion 20 is a portion onto which the notches 42A and 44A of the sensor cartridge 1 engage, and comprises a pair of recessed portions 24 and 25. These recessed portions 24 and 25 each have a tapering face 24a or 25a and guide faces 24b or 25b. The distance between the guide faces 24b or 25b of each of the recessed portions 24 and 25 spreads out toward the edge for a portion near to the edge, and corresponds to the distance between the second member 42 and the plate-shaped portion 44 of the first member 41 of the case 4 for a portion far from the edge. Moreover, the slope of the tapering faces 24a and 25a of the recessed portions 24 and 25 corresponds to the slope of the tapering faces 42Ab and 44Ab of the notches 42A and 44A in the case 4. Consequently, when the sensor cartridge 1 is to be installed onto the analyzer 2, because the portion of each of the recessed portions 24 and 25 near to the edge opens out toward the edge, alignment of the notches 42A and 44A of the sensor cartridge 1 can be carried out easily, and moreover for the holding portion 20, the notches 42A and 44A of the sensor cartridge 1 and the recessed portions 24 and 25 of the holding portion 20 can easily be fitted together. At this time, movement in the thickness direction of the analyzer 2 is restricted by the notches 42A and 44A, and moreover movement in the thickness direction of the sensor cartridge 1 is restricted by the guide faces 24b and 25b of the recessed portions 24 and 25. As a result, the sensor cartridge 1 is fixed properly positioned onto the analyzer 2.

The inserting portion 21 is formed between the recessed portions 24 and 25 of the holding portion 20, and has therein a holding space 26 in which can be housed an end portion of a biosensor 3. A projection 27a that projects out downward is formed on an upper wall face 27 defining the holding space 26. This projection 27a fits into the recess 35 of the biosensor 3 when the biosensor 3 has been inserted into the holding space 26 as shown in FIGS. 7C and 7D. As a result, the biosensor 3 is kept installed in the analyzer 2. Furthermore, a plurality of terminals 28 (in the drawings only one terminal 28 is shown) extend out into the holding space 26. The plurality of, for example four, terminals 28 are disposed in positions corresponding to the end portions 36a to 38a of the electrodes 36 to 38. Each terminal 28 is biased downward. Consequently, when a biosensor 3 has been inserted into the holding space 26, the substrate 30 of the biosensor 3 is sandwiched between the terminals 28 and a lower wall face 29 defining the holding space 26. At this time, the plurality of terminals 28 contact the end portions 36a to 38a of the electrodes 36 to 38.

A biosensor 3 is installed into the analyzer 2 using the sensor cartridge 1 through the following operations.

First, as shown in FIG. 7A, the sensor cartridge 1 is located and fixed onto the analyzer 2. As described above, this locating and fixing is carried out by fitting the notches 42A and 44A of the sensor cartridge 1 onto the holding portion 20 of the analyzer 2. At this time, the slit 46 of the sensor cartridge 1 (the case 4) and the inserting portion 21 of the analyzer 2 are also aligned with one another.

Next, a biosensor 3 is discharged from the sensor cartridge 1 following the procedure described earlier with reference to FIGS. 5A and 5B, whereby the biosensor 3 is installed in the analyzer 2. More specifically, the knob 50 of the sensor cartridge 1 is moved in the direction of the arrow B by, for example, a manual operation of a user, whereby the biosensor 3 moves in the direction of the arrow B, and is discharged from the sensor cartridge 1. At this time, as shown in FIG. 7B, the biosensor 3 is inserted from an end portion 30b thereof into the inserting portion 21 of the analyzer 2. Upon moving the biosensor 3 further in the direction of the arrow B, as shown in FIG. 7C, the end portion 30a of the substrate 30 is sandwiched between the terminals 28 and the lower wall face 29, and moreover the projection 27a engages into the recess 35 in the biosensor 3. With the biosensor 3 fixed in the analyzer 2 in this way, the sensor cartridge 1 is separated away from the analyzer 2 in the direction of the arrow A as shown in FIG. 7D, whereby the biosensor 3 is installed in the analyzer 2.

Moving on, concentration measurement with the analyzer 2 (see FIGS. 3 and 4) is carried out by supplying a specimen liquid onto the biosensor 3 via the specimen introduction port 33a. The specimen liquid introduced in from the specimen introduction port 33a travels through the channel 33 toward the air release port 33b. At this time, a specific component in the specimen liquid reacts with the reagent layer 39, and hence the mediator is reduced or oxidized. If a voltage is applied to the reagent layer 39 via the end portions 36a and 37a, then electron transfer between the working electrode 36 and the mediator then takes place. The amount of this electron transfer is measured by the analyzer 2 using the working electrode 36 and the counter electrode 37. This amount of electron transfer correlates to the concentration of the specific component, and hence the concentration of the specific component can be calculated by measuring the amount of electron transfer. Regarding the detecting electrodes 38, on the other hand, by measuring the amount of electron transfer for these electrodes, it can be detected whether the specimen liquid has been supplied onto the biosensor 3.

With the present embodiment, a biosensor 3 can be installed in the analyzer 2 merely by locating and fixing the sensor cartridge 1 onto the analyzer 2 and then moving the knob 50. The locating and fixing of the sensor cartridge 1 onto the analyzer 2 can be carried out easily utilizing the notches 42A and 44A of the sensor cartridge 1 and the recessed portions 24 and 25 of the analyzer 2, and moreover the operation of moving the knob 50 is also extremely easy. In this way, with the present embodiment, a biosensor 3 can be installed in the analyzer 2 through extremely simple operations, and hence a biosensor 3 can be installed with no problems even by people with failing eyesight or elderly people.

The present invention is not limited to the present embodiment, but rather various design modifications are possible. For example, regarding the sensor cartridge 1, as shown in FIGS. 8A and 8B, instead of an operating belt in the form of a loop, an operating belt 5' in the form of a band may be used, and as shown in FIGS. 9A and 9B, the members for moving a biosensor 3 and the member for opening and closing the slit 46 in the case 4 may be formed as separate bodies.

Figure 8A:
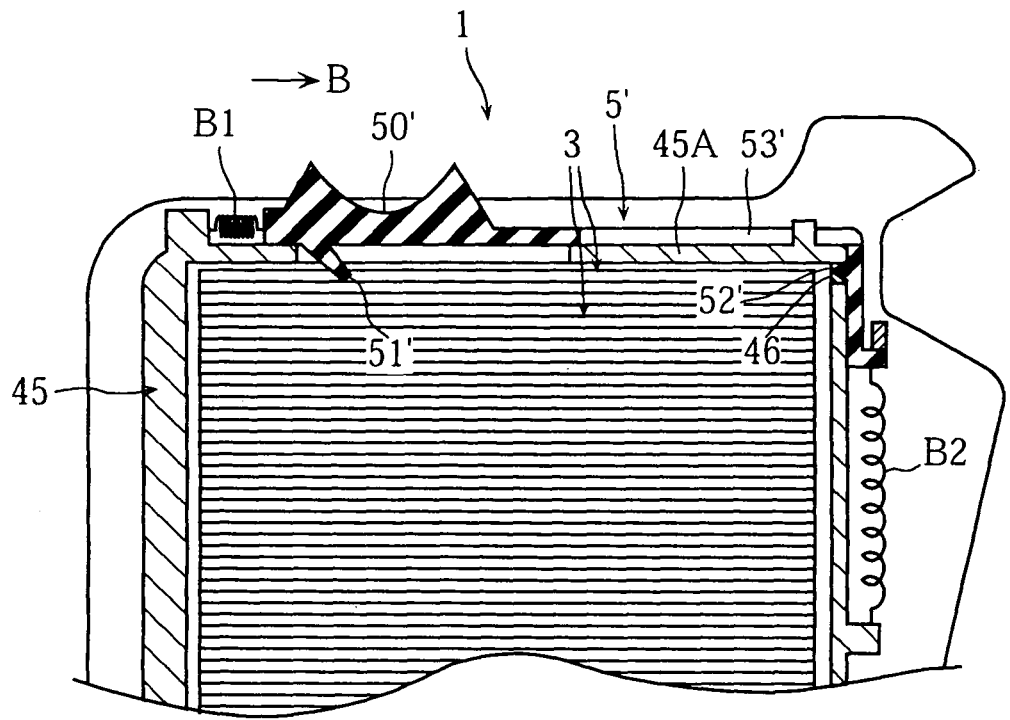
FIGS. 8A and 8B are sectional views of main parts for explaining another example of an operating belt in the sensor cartridge.
Figure 8B:
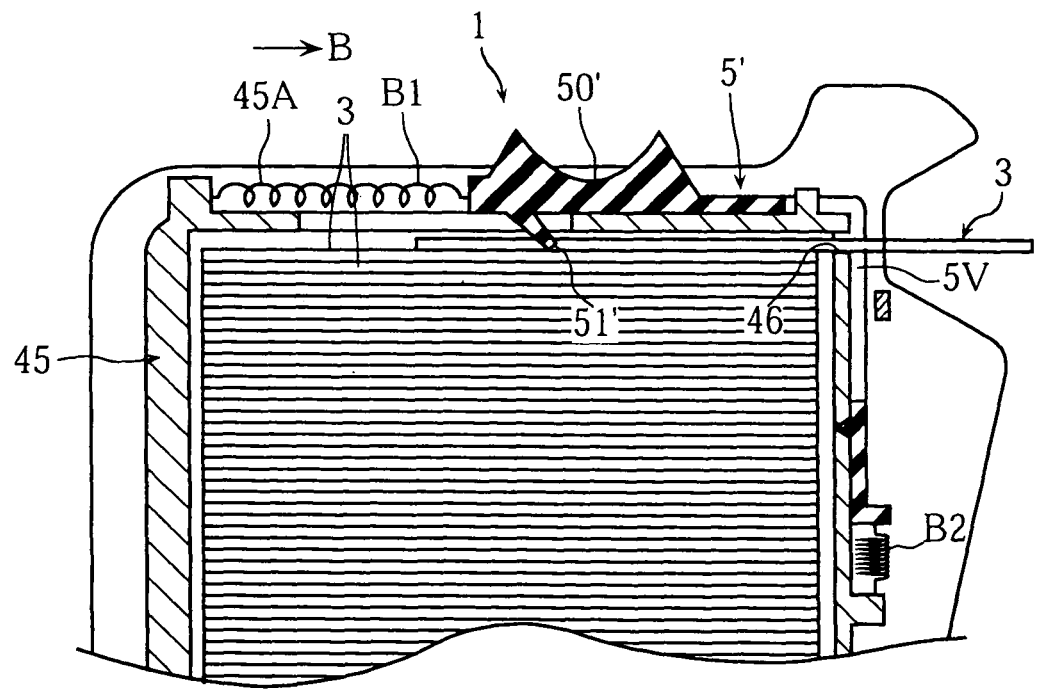

In the example shown in FIGS. 8A and 8B, a part from the operating belt 5' being formed in the form of a band, the operating belt 5' has a similar constitution to the operating belt 5 described earlier; the operating belt 5' is provided so as to cover the slit 46 and the upper wall portion 45A of the annular wall portion 45. The two ends of the operating belt 5' are fixed to the annular wall portion 45 of the case 4 by coil springs B1 and B2. In a natural state, the slit 46 is closed up by a closing portion 52', and engaging claws 51' are engaged into the recess 34 of a biosensor 3. When a knob 50' is moved in the direction of the arrow B in the drawings by a manual operation of a user or the like, the biosensor 3 moves in the direction of the arrow B, and moreover an opening portion 53' comes to be positioned in a place corresponding to the slit 46, and hence the slit 46 is opened up. As a result, the biosensor 3 is discharged from the slit 46. If the force acting on the operating belt 5' is then released, the operating belt 5' then automatically returns to its natural state through the forces of the springs.

Figure 9A:
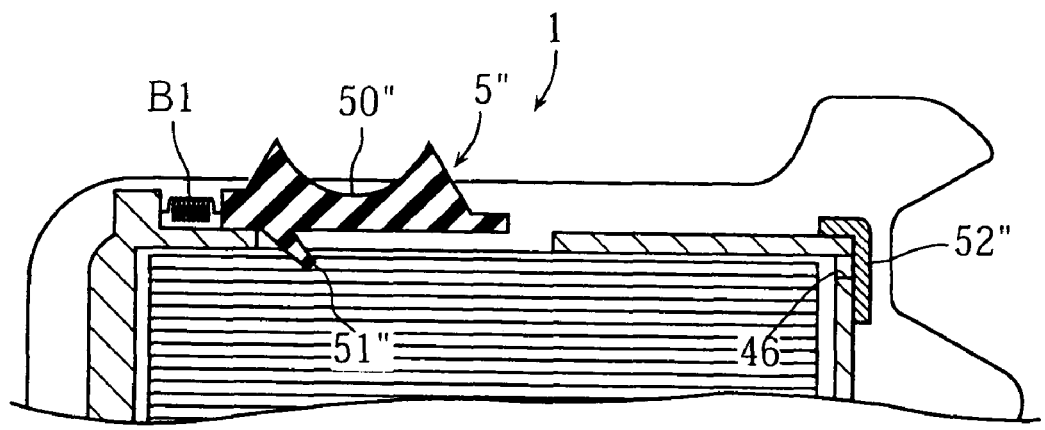
FIGS. 9A and 9B are sectional views of main parts for explaining an example in which members for moving a biosensor and a notch opening/closing member are constituted as separate bodies in the sensor cartridge.
Figure 9B:
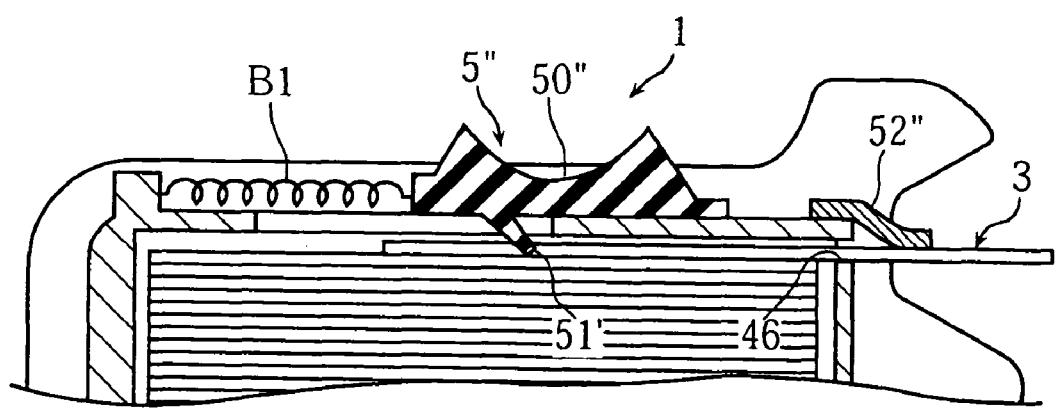

On the other hand, in the example shown in FIGS. 9A and 9B, an operating belt 5" having a knob 50" and engaging claws 51" integrally molded thereon is fixed to the annular wall portion 45 of the case 4 by a spring B1. The slit 46 in the case 4 is closed up by a curtain 52". If the operating belt 5" is moved, then a biosensor 3 is pushed out from the case 4 while pushing the curtain 52" out of the way. If the force acting on the knob 50" is released, the operating belt 5" then automatically returns to its original position through the elastic force of the spring B1.

Figure 10A:
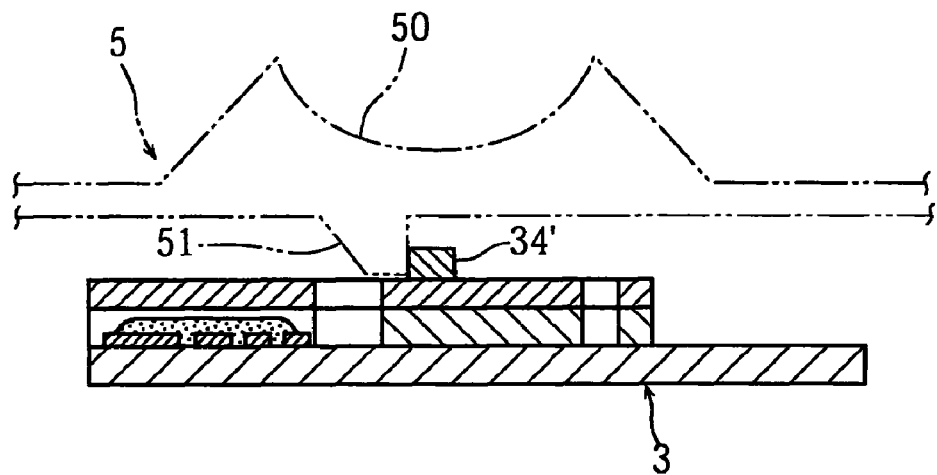
FIGS. 10A to 10C are sectional views showing another example of a method of retrieving a biosensor from the sensor cartridge.
Figure 10B:
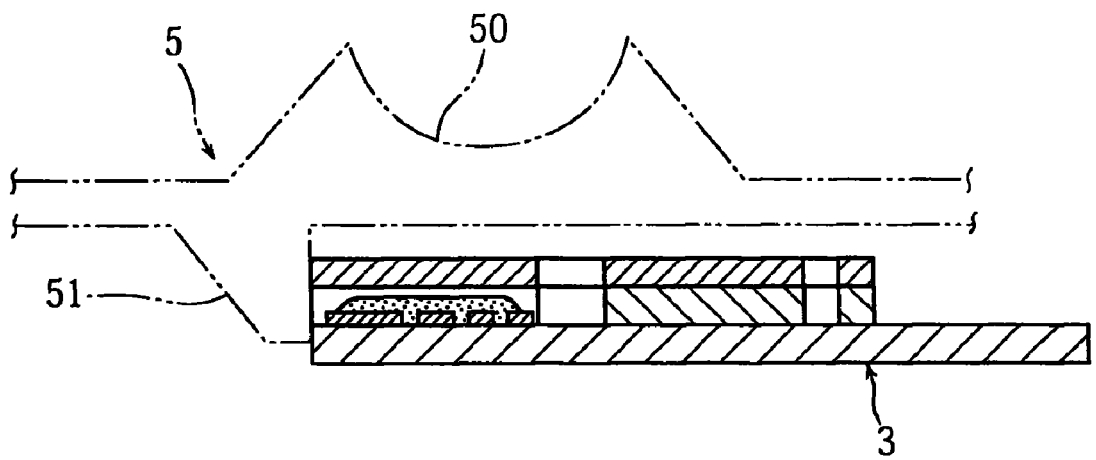
Figure 10C:
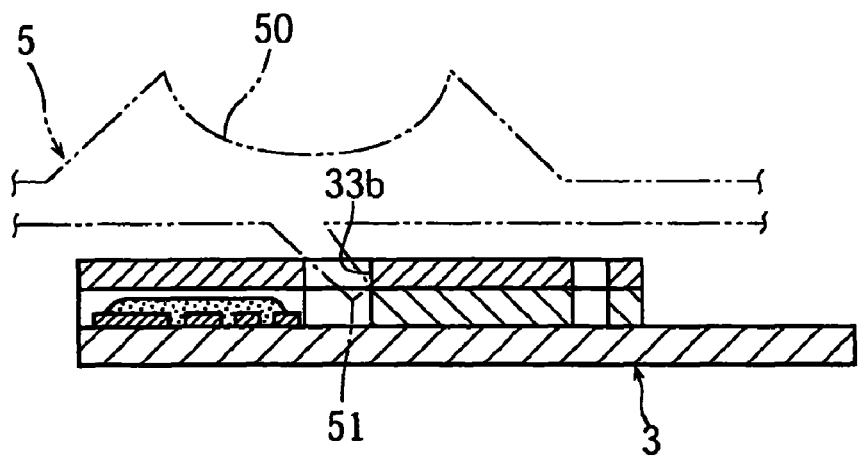
Figure 11:
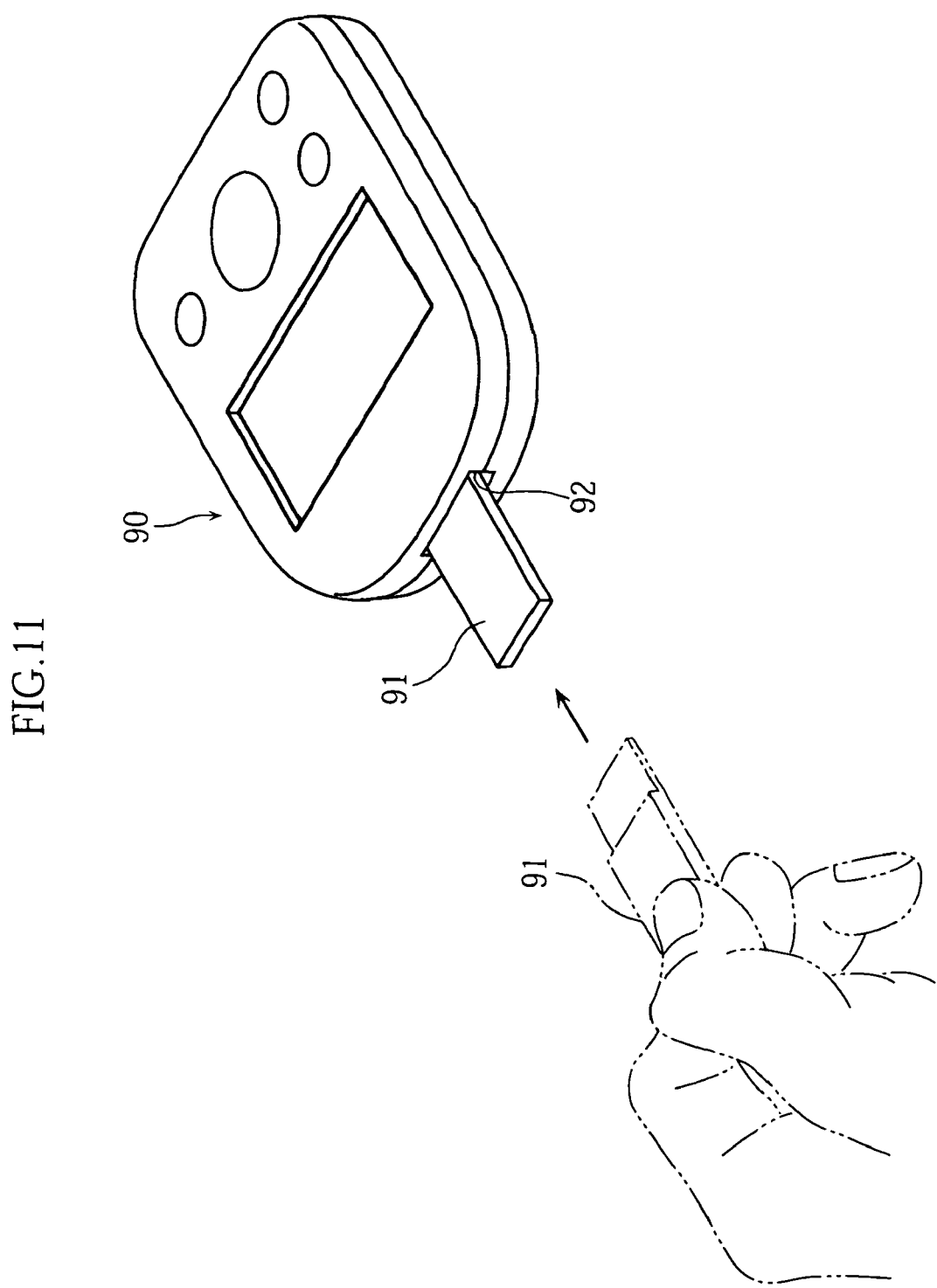
FIG. 11 is an overall perspective view for explaining a conventional operation of installing a biosensor into an analyzer.

Moreover, regarding the method of moving a biosensor 3 through the movement of the knob 50, design modification is possible as shown, for example, in FIGS. 10A to 10C. FIG. 10A shows an example in which a projection 34' is provided on the biosensor 3, and the biosensor 3 is moved through the engaging claws 51 pushing the projection 34', FIG. 10B shows an example in which the biosensor 3 is moved through the engaging claws 51 pushing a rear end of the biosensor 3, and FIG. 10C shows an example in which the engaging claws 51 engage into the air release port 33b provided in the biosensor 3, and the biosensor 3 is moved in this state.

Moreover, various design modifications are also possible with regard to the method of locating and fixing the sensor cartridge onto the analyzer, or fixing a biosensor in the analyzer. For example, it is possible to provide a recess in the inserting portion of the analyzer, and provide a projection that engages into this recess on each biosensor.

The invention claimed is:

1. An analytical tool cartridge comprising:
a case including a storage space and a retrieval port that communicates the storage space with an external space;
a plurality of analytical tools stored in the storage space in a stacked state;
a retrieval mechanism for retrieving the analytical tools one at a time from the case via the retrieval port;
and an opening/closing mechanism for opening and closing the retrieval port;
wherein the retrieval mechanism and the opening/closing mechanism are integral with each other as a single operating body,
wherein the operating body is formed in a loop encircling the plurality of analytical tools and comprises an engaging projection, a closing portion and an opening portion, the engaging projection being configured to integrally move the analytical tools when the operating body is moved in a specific direction from a standby state, the closing portion being configured to close up the retrieval port in the standby state, the opening portion being configured to open up the retrieval port when the operating body is moved in the specific direction from the standby state.

2. The analytical tool cartridge according to claim 1, wherein the case includes an annular wall portion that defines the storage space and has the retrieval port provided therein, the operating body being disposed along an outer surface of the annular wall portion, and movable relative to the annular wall portion.

3. The analytical tool cartridge according to claim 1, wherein the analytical tools each include an engaging portion with which the engaging projection engages.

4. The analytical tool cartridge according to claim 1, wherein the operating body includes an operating portion for applying a load to and thus moving the operating body.

5. The analytical tool cartridge according to claim 1, wherein the storage space has a desiccant housed therein.

6. The analytical tool cartridge according to claim 5, wherein the analytical tools are stored in the storage space in a state supported by a platform, the desiccant being fixed to the platform.

7. The analytical tool cartridge according to claim 1, wherein the analytical tools are stored in the storage space in a state supported by a platform, and are supported in a state biased by the platform.

8. The analytical tool cartridge according to claim 1, wherein the case is provided with a guiding portion for guiding the operating body when the operating body is moved.

9. The analytical tool cartridge according to claim 1, wherein the storage space has therein stacked on top of the analytical tools an information outputting chip from which can be outputted information relating to properties of the analytical tools.

10. The analytical tool cartridge according to claim 9, wherein the information outputting chip outputs information relating to a calibration curve.

11. A set of an analytical tool cartridge and an analyzer, the analytical tool cartridge comprising:
a case including a storage space and a retrieval port that communicates the storage space with an external space;
a plurality of analytical tools stored in the storage space in a stacked state;

a retrieval mechanism for retrieving the analytical tools one at a time from the case via the retrieval port;

and an opening/closing mechanism for opening and closing the retrieval port;

wherein the retrieval mechanism and the opening/closing mechanism are integral with each other as a single operating body, and wherein the operating body is formed in a loop encircling the plurality of analytical tools and comprises an engaging projection, a closing portion and an opening portion, the engaging projection being configured to integrally move the analytical tools when the operating body is moved in a specific direction from a stand by state, the closing portion being configured to close up the retrieval port in the standby state, the opening portion being configured to open up the retrieval port when the operating body is moved in the specific direction from the standby state, the analyzer being constituted so as to have installed therein an analytical tool retrieved from the analytical tool cartridge, and analyze a specific component in a specimen liquid supplied onto the analytical tool, at least one of the analytical tool cartridge and the analyzer being provided with cartridge fixing means for locating and fixing the analytical tool cartridge onto the analyzer.

12. The set of an analytical tool cartridge and an analyzer according to claim 11, wherein the cartridge fixing means includes first stopper faces for restricting movement of the analytical tool cartridge in a direction orthogonal to each of a direction of stacking of the analytical tools and a direction of insertion of the analytical tools, and second stopper faces for restricting movement of the analytical tool cartridge in the direction of stacking of the analytical tools.

13. The set of an analytical tool cartridge and an analyzer according to claim 12, wherein the first stopper faces are provided on the analyzer, the second stopper faces being provided on the analytical tool cartridge.

14. The set of an analytical tool cartridge and an analyzer according to claim 13, wherein the cartridge fixing means is constituted from notches provided in the case, and recessed portions provided in the analyzer.

15. A set of an analytical tool cartridge and an analyzer, the analytical tool cartridge comprising:

a case including a storage space and a retrieval port that communicates the storage space with an external space;

a plurality of analytical tools stored in the storage space in a stacked state;

a retrieval mechanism for retrieving the analytical tools one at a time from the case via the retrieval port; and an opening/closing mechanism for opening and closing the retrieval port;

wherein the retrieval mechanism and the opening/closing mechanism are integral with each other as a single operating body, wherein the operating body is formed in a loop encircling the plurality of analytical tools and comprises an engaging projection, a closing portion and an opening portion, the engaging projection being configured to integrally move the analytical tools when the operating body is moved in a specific direction from a standby state, the closing portion being configured to close up the retrieval port in the standby state, the opening portion being configured to open up the retrieval port when the operating body is moved in the specific direction from the standby state, the analyzer being constituted so as to install an analytical tool retrieved from the analytical tool cartridge, and to analyze a specific component in a specimen liquid supplied onto the analytical tool, the analyzer including an inserting portion into which an end portion of the analytical tool is inserted, the analytical tool cartridge and the inserting portion being provided with analytical tool fixing means for fixing the analytical tool in the analyzer.

16. The set of an analytical tool cartridge and an analyzer according to claim 15, wherein the analytical tool fixing means comprises a projection provided on one of the analytical tool and the inserting portion, and a recess provided in the other thereof for engaging with the projection.

* * * * *